United States Patent [19]

Yamahara et al.

[11] 4,071,569
[45] Jan. 31, 1978

[54] PROCESS FOR PRODUCING PHENOLS

[75] Inventors: Takeshi Yamahara, Chiba; Tetsuo Takano, Takatsuki; Mitsuhisa Tamura, Osaka; Hiroshi Yoshihara, Takatsuki, all of Japan

[73] Assignee: Sumitomo Chemical Company, Limited, Osaka, Japan

[21] Appl. No.: 680,445

[22] Filed: Apr. 26, 1976

[30] Foreign Application Priority Data

| May 2, 1975 | Japan | 50-53481 |
| May 23, 1975 | Japan | 50-62321 |
| June 4, 1975 | Japan | 50-67763 |

[51] Int. Cl.² .................. C07C 39/06; C07C 39/12
[52] U.S. Cl. .................. 260/621 C; 260/619 R; 260/624 R; 260/622 R; 260/626 R; 260/613 D
[58] Field of Search .......... 260/621 C, 610 B, 612 D, 260/619 R, 620, 620 R, 624 R, 626 R, 622 R, 613 R

[56] References Cited

U.S. PATENT DOCUMENTS

| 2,626,281 | 1/1953 | Joris | 260/593 R |
| 2,668,859 | 2/1954 | Seriabine | 260/593 R |
| 2,853,532 | 9/1958 | De Jong | 260/6 |
| 3,497,561 | 2/1970 | Gelbein | 260/606 |
| 3,928,469 | 12/1975 | Suda | 260/621 C |

*Primary Examiner*—Bernard Helfin
*Assistant Examiner*—W. B. Lone
*Attorney, Agent, or Firm*—Stevens, Davis, Miller & Mosher

[57] ABSTRACT

Phenols can be produced in a high yield together with useful aldehydes by cleaving a secondary alkylbenzene hydroperoxide in the presence of sulfur, a sulfur oxide or a phosphorus sulfide and then separating the desired phenols from the cleavage product.

4 Claims, No Drawings

PROCESS FOR PRODUCING PHENOLS

The present invention relates to a process for producing phenols by cleaving a secondary alkylbenzene hydroperoxide. More particularly, the invention pertains to a process for producing phenols which comprises cleaving a secondary alkylbenzene hydroperoxide in the presence of a catalyst.

Various processes for the production of phenols are well known in the art. A process has heretofore been carried out which comprises oxidizing a tertiary alkylbenzene to the corresponding hydroperoxide and then cleaving said hydroperoxide in the presence of an acid catalyst such as sulfuric acid to obtain a mixture consisting of a phenol and a ketone. For example, a process for producing phenol by the catalytic cleavage of cumene hydroperoxide is carried out on a commercial scale. It has been reported that this process gives a yield of phenol of about 90 mole % and a yield of acetone of about 85 mole % based on the amount of the hydroperoxide, but the process is still unsatisfactory as a commercial process in that:

1. The step of separating phenol is complicated since a considerable amount of a high molecular weight resinous by-product is formed together with the desired phenol and acetone.
2. A plant using an acid catalyst usually requires an expensive corrosion resistant material.
3. It is necessary to remove the acid catalyst or neutralize the acid catalyst with an alkali and then treat the resulting salt before phenol is separated from the cleavage product.

Although the above-mentioned process gives acetone together with phenol, the realization of a process for the production of phenol which permits the production of a useful compound other than acetone in a high yield together with phenol is desirable. However, the cleavage of hydroperoxides other than tertiary alkylbenzene hydroperoxides has not been regarded as a commercially attractive process owing to a low yield of phenols.

The present inventors have studied to find an economical process for the production of phenols by the cleavage of secondary alkylbenzene hydroperoxides.

According to the present invention, there is provided a process for producing phenols by cleaving a secondary alkylbenzene hydroperoxide which comprises the step of carrying out the cleavage in the presence of a catalyst selected from the group consisting of sulfur, sulfur oxides and phosphorus sulfides and the step of separating the desired phenol from the cleavage product.

The sulfur used as a catalyst may be in any state of solid and liquid and in any allotropic modification. As the sulfur, either natural sulfur or purified sulfur obtained by a commercial process of production may be used.

The phosphorus sulfides include diphosphorus pentasulfide ($P_2S_5$), tetraphosphorus heptasulfide ($P_4S_7$), tetraphosphorus pentasulfide ($P_4S_5$) and tetraphosphorus trisulfide ($P_4S_3$). Among these compounds diphosphorus pentasulfide is particularly preferable. The specific examples of sulfur oxides include sulfur dioxide ($SO_2$), disulfur trioxide ($S_2O_3$), sulfur trioxide ($SO_3$), and sulfur tetroxide ($SO_4$). Among these compounds sulfur dioxide and sulfur trioxide are particularly preferable.

Of these catalysts used in the present invention, sulfur is most favorable to produce phenols in a high yield with little production of a high molecular weight resinous by-products without anxiety regarding corrosion.

These catalysts may be either added alone to the reaction system or added as a solution thereof in a suitable organic solvent such as acetone, methyl isobutyl ketone, benzene, toluene, ethylbenzene, xylenes, cumenes, diisopropylbenzenes, chlorobenzene, nitrobenzene and diethylbenzenes. The amount of the catalyst used in the process of the present invention may be as small as up to 10% by weight based on the weight of the hydroperoxide. The amount of the catalyst used in preferable examples of the present invention is 0.001 to 5% by weight based on the weight of the hydroperoxide.

The hydroperoxides used in the present invention include secondary mono- and di-hydroperoxides of alkylbenzenes of the formula,

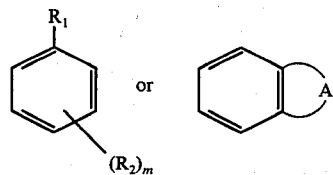

wherein $R_1$ is ethyl, $\beta$-phenylethyl, benzyl, or $-C_nH_{2n+1}$ in which $n$ is an integer of 3 to 12, $R_2$ is hydrogen, $C_1$-$C_8$ alkyl, $C_1$-$C_6$ alkoxy or nitro, $m$ is an integer of 1 to 3 and A is $C_3$-$C_5$ alkylene.

Of these hydroperoxides, ethylbenzene hydroperoxide, $\beta$-phenylethylbenzene hydroperoxide, diphenylmethane hydroperoxide, diethylbenzene monohydroperoxides and diethylbenzene dihydroperoxides are favorably used. Among these alkylbenzene hydroperoxides ethylbenzene hydroperoxide is most preferable from a commercial point of view. In this case, phenol and acetaldehyde are obtained. Other favorable hydroperoxides are diethylbenzene monohydroperoxides. In this case, ethylphenol and acetaldehyde can be obtained in a high yield. Alternatively, it is possible to use dialkylbenzene dihydroperoxides. In this case, so-called dihydric phenols can be obtained. Such dihydroperoxides may contain at least one substituent in their aromatic nucleus. In this case, the corresponding so-called substituted dihydric phenols can be obtained.

The secondary alkylbenzene hydroperoxides used as a starting material in the process of the present invention can be synthesized by usual processes, for example, by the autoxidation of an alkylbenzene. The secondary hydroperoxides obtained by such processes can be used without any further purification. Thus, the crude alkylbenzene hydroperoxides containing by-products formed in the course of oxidation can be subjected to the cleavage reaction.

The preferable range of the cleavage reaction temperature in the practice of the process of the present invention is room temperature to 200° C, and preferably 60° to 180° C, and further preferably 120° to 180° C. It is advantageous to carry out the cleavage at a controlled temperature by cooling the reaction mixture to absorb part or all of the heat generated due to the exothermic reaction so that the temperature may not increase remarkably.

The reaction pressure varies according to the form of the reactor used and operation conditions, but is generally atmospheric pressure to 10 kg/cm². It is also possible to carry out the cleavage under reduced pressure to remove the aldehydes from the reaction system so that the undesirable reaction between the aldehydes and the other components of the cleavage product may be avoided.

The reaction time varies according to the reaction temperature, the concentration of the catalyst, the concentration of the hydroperoxide, etc., but is usually 1 minute to 1 hour. At a preferable range of the reaction temperature of, for example, 120° to 180° C, the reaction time is suitably 3 to 30 minutes.

In the practice of the process of the present invention, it is usual to carry out the cleavage in an inert solvent, that is, a solvent which does not react with the hydroperoxides and the cleavage product. The inert solvent is exemplified by benzene, toluene, ethylbenzene, xylenes, diethylbenzenes, cymenes, diisopropylbenzenes, chlorobenzene and nitrobenzene. The amount of the secondary alkylbenzene hydroperoxide contained in these solvents is preferably 5 to 30% by weight.

The cleavage of the alkylbenzene hydroperoxides in the process of the present invention can be practiced by either batch process or continuous process and is not restricted to any special type.

The separation of the phenols and aldehydes produced by the process of the present invention from the reaction product may be carried out by usual processes, for example, fractional distillation. Alternatively, if desired, it is possible to separate and recover the desired product after converting a small amount of the by-products such as acetophenone or α-phenylethyl alcohol into ethylbenzene according to the process as described in, for example, Japanese Patent Kakai (Laid Open) No. 116,430/1975.

The most surprising characteristic of the process of the present invention resides in the fact that the yield of a phenol from the secondary alkylbenzene hydroperoxide is remarkably higher than the yield obtained in the case where an acid catalyst is used. For example, the yield of phenol from ethylbenzene hydroperoxide obtained according to the process of the present invention exceeds 90 mole %. Since phenol can be obtained in such a high yield, the amount of a high molecular weight resinous by-product produced remarkably decreases as compared with the processes using a prior art acid catalyst. Further, since a strong acid is not used as a catalyst, a reactor made of a special corrosion resistant material is not required for the cleavage of the hydroperoxide. Also, a complex step, the neutralization treatment of an acid catalyst prior to the step of the separation of phenols can be remarkably simplified.

In order that those skilled in the art may better understand how the present invention can be practiced, the following examples are given by way of illustration and not by way of limitation. The analysis of the raw materials and products in the examples was carried out by infrared spectrophotometry, gas chromatography, high performance liquid chromatography and idometry. The selectivity in the examples is represented as mole % based on the amount of the hydroperoxide.

EXAMPLE 1

Into a 2cc-volume pressure-tight glass ampoule were charged 1 cc of a solution of 10.2% by weight of ethylbenzene hydroperoxide in ethylbenzene and 0.3 mg of sulfur. The ampoule was tightly stoppered and then dipped in an oil bath at 150° C for about 3 minutes. After the completion of the generation of bubbles by the reaction was confirmed, the ampoule was removed from the oil bath and cooled thoroughly in water. The analysis of the product was then carried out. As a result, the conversion of the ethylbenzene hydroperoxide, the yield of phenol and the yield of acetaldehyde were 100%, 97.4% and 92.5%, respectively. No of resinous substance in the reaction liquid was observed.

EXAMPLES 2 – 6

The reaction was carried out by using various secondary alkylbenzene hydroperoxides and various catalysts in the same manner as in Example 1. The results obtained are shown in the following table.

Table

| Example | Starting material | | | | Catalyst | |
|---|---|---|---|---|---|---|
| | Hydroperoxide (HPO) | Process of preparation | Concentration[1] (% by weight) | Amount charged (cc) | Substance | Amount added (mg) |
| 2 | Ethylbenzene HPO | $H_2O_2$ oxidation | 7.5 | 1.0 | Diphosphorus pentasulfide ($P_2S_5$) | 2.4 |
| 3 | " | " | 19.8 | 1.0 | Sulfur dioxide ($SO_2$) | 3.0 |
| 4 | " | " | 19.8 | 1.0 | Sulfor trioxide ($SO_3$) | 0.6 |
| 5 | p-Diethylbenzene mono HPO | " | 12.4 | 1.0 | Sulfur (S) | 0.3 |
| 6 | Ethylbenzene HPO | Air oxidation | 10.3 | 1.0 | " | 0.3 |

| Reaction conditions | | Reaction results | | |
|---|---|---|---|---|
| Temperature (° C) | Time (min.) | HPO conversion (%) | Selectivity to phenols (%) | Selectivity to aldehydes (%) |
| 150 | 3.0 | 100 | 91.8 | — |
| 150 | 2.5 | 100 | 92.4 | — |
| 150 | 3.0 | 100 | 87.6 | — |
| 160 | 3.0 | 100 | 99.3[2] | 86.5 |
| 150 | 3.0 | 100 | 90.2 | 82.4 |

Notes:
[1] Used ethylbenzene as solvent in all cases.
[2] p-Ethylphenol.

EXAMPLE 7

Into a glass tubular reactor having an inner diameter of 1.5 mm and a length of 2.4 m was fed continuously an ethylbenzene solution comprising 7.5% by weight of ethylbenzene hydroperoxide and 250 ppm of sulfur at a rate of 30 cc per hour. A pressure regulating valve controlled at 5 kg/cm² was provided on the exit side of the reactor. The whole reactor was dipped in an oil bath at 150° C. The solution which had passed through the reactor was thoroughly cooled, and the analysis of the reaction product was carried out. As a result, the conversion of the ethylbenzene hydroperoxide and the yield of phenol were 100% and 97.1%, respectively. The formation of any resinous substance was hardly observed.

What is claimed is:

1. In the process for producing a phenol by cleaving a secondary alkylbenzene hydroperoxide selected from the group consisting of mono- and di-hydroperoxides of alkylbenzenes of the formula

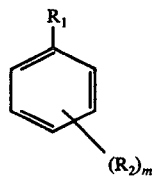

wherein $R_1$ is ethyl, $\beta$-phenylethyl, benzyl or $-C_nH_{2n+1}$ in which $n$ is an integer of 3 to 12, $R_2$ is hydrogen, $C_1-C_8$ alkyl, $C_1-C_6$ alkoxy or nitro, and $m$ is an integer of 1 to 3, and monohydroperoxides of alkylbenzenes of the formula

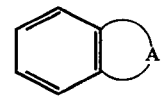

wherein A is $C_3-C_5$ alkylene, which comprises dissolving said secondary alkylbenzene hydroperoxide in an organic solvent which is inert to both the hydroperoxide and the cleavage product to form a solution, heating the solution in the presence of a catalyst at a temperature of 60° to 180° C and separating the desired phenol from the cleavage product, the said solution containing 5 to 30% by weight of the secondary alkylbenzene hydroperoxide, the improvement comprising using sulfur as said catalyst in an amount of 0.001 to 5% by weight based on the weight of the secondary alkylbenzene hydroperoxide.

2. A process according to claim 1, wherein the hydroperoxide is ethylbenzene hydroperoxide, $\beta$-phenylethylbenzene hydroperoxide, diphenylmethane hydroperoxide, diethylbenzene monohydroperoxides or diethylbenzene dihydroperoxides.

3. A process according to claim 1, wherein said organic solvent is selected from the group consisting of benzene, toluene, ethylbenzene, xylenes, diethylbenzenes, cymenes, diisopropylbenzenes, chlorobenzene and nitrobenzene.

4. A process according to claim 1, wherein the heating is conducted at a temperature of 120° to 180° C.

* * * * *